United States Patent
Zadi (10) Patent No.: US 7,025,988 B2
(45) Date of Patent: Apr. 11, 2006

(54) LIPOSOMES

(75) Inventor: Brahim Zadi, London (GB)

(73) Assignee: Lipoxen Technologies Limited, London (GB)

( * ) Notice: Subject to any disclaimer, the term of this patent is extended or adjusted under 35 U.S.C. 154(b) by 400 days.

(21) Appl. No.: 10/182,921

(22) PCT Filed: Jan. 31, 2001

(86) PCT No.: PCT/GB01/00391

§ 371 (c)(1),
(2), (4) Date: Oct. 7, 2002

(87) PCT Pub. No.: WO01/56548

PCT Pub. Date: Aug. 9, 2001

(65) Prior Publication Data

US 2003/0138481 A1    Jul. 24, 2003

(30) Foreign Application Priority Data

Feb. 4, 2000    (EP)  ................... 00300904

(51) Int. Cl.
*A61K 9/127*    (2006.01)

(52) U.S. Cl. ............... 424/459; 264/4.1; 264/4.3; 264/4.6

(58) Field of Classification Search ............ 424/450, 424/1.21, 9.321, 9.51; 264/4.1, 4.3
See application file for complete search history.

(56) References Cited

U.S. PATENT DOCUMENTS

| 4,885,172 A | 12/1989 | Bally et al. |
| 5,653,998 A | 8/1997 | Hamann et al. |
| 5,683,715 A | 11/1997 | Boni et al. |
| 6,322,809 B1 * | 11/2001 | Gregoriadis et al. ........ 424/450 |

FOREIGN PATENT DOCUMENTS

| EP | 0 700 679 A1 | 3/1996 |
| FR | 2593394 * | 7/1987 |
| WO | WO 86/01103 A1 | 2/1986 |
| WO | WO 87/01933 A1 | 4/1987 |
| WO | WO 99/65465 A1 | 12/1999 |

* cited by examiner

Primary Examiner—Gollamudi S. Kishore
(74) Attorney, Agent, or Firm—Dickstein, Shapiro, Morin & Oshinsky, LLP.

(57) ABSTRACT

Liposomes containing lipophilic active ingredient are produced by dehydrating a mixture of liposomes, lipophilic active ingredient and sugar, usually followed by a rehydration step to form dehydration-rehydration vesicles. The lipophilic drug is suitably paclitaxel. The sugar is usually sucrose. The liposome forming compounds preferably include cholesterol and phosphatidylcholine, and optionally an anionic lipid. The ratio of sugar:lipid is preferably at least 5:1 w/w. The ratio of lipid:drug is preferably (up to 10):1 w/w.

21 Claims, 2 Drawing Sheets

Lipid ($^{14}$C radioactivity) levels in total plasma.

Fig1. Paclitaxel ($^3$H radioactivity) levels in total plasma.

Fig. 2. Lipid ($^{14}$C radioactivity) levels in total plasma.

LIPOSOMES

The present invention relates to liposomes and methods for forming liposomes, as well as their use, in particular in pharmaceutical applications. In particular the invention relates to liposomes containing active ingredients which are lipophilic, of particular utility for formulating paclitaxel and analogues and derivatives thereof.

Paclitaxel is an antimicrotubule agent which has shown promising clinical activity against a wide variety of tumours, including ovarian, breast and lung, as well as melanomas and lymphomas. Derivatives of paclitaxel have also been described having analogous properties. Paclitaxel may be isolated from its natural source (Yew trees), or synthetically produced.

Paclitaxel has a very low solubility in conventional aqueous vehicles. The only preparation approved for clinical use consists of a solution in the vehicle Cremophor EL which is a 50:50 mixture of ethanol and ethoxylated caster oil. The paclitaxel/Cremophor mixture is diluted prior to being infused. One problem is that the diluted mixture is unstable and paclitaxel tends to precipitate, necessitating the use of a filter in line, and resulting in loss of active. Furthermore the organic vehicle produces toxic side effects including an anaphylaxis and pain at the site of injection. Tests on mice indicate a low maximum tolerable dose.

Various ways of improving the dispersability of paclitaxel into aqueous vehicles have been devised. Phosphate derivatives with improved solubility have been made by Ueda, Y. et al in Bioorg. Med. Chem. Lett. 3(1993), 1761–66 and Vyas, D. M. et al in Bioorg. Med. Chem. Lett. 3(1993) 1357–60. Paclitaxel has been sialylated to render it more soluble by Takahashi, T. et al in Bioorg. Med. Chem. Lett. 8 (1998) 113–116. It has been complexed with cyclodextrins by Sharma, U. S. et al in J. Pharm. Sci. 84(10) (1995) 1123–30. Other prodrugs of Taxol have been described by Mathew, A. E. et al in J. Med. Chem 35(1992) 145–151 and by Deutsch, H. et al in J. Med. Chem. 32(1989) 788–792.

Paclitaxel has also been encapsulated into liposomes. Rahman, A et al in U.S. Pat. Nos. 5,424,073, 5,648,090 and (as Cabanes, A. et al) in Int. J. Onc. 12 (1998) 1035–40 describe a process in which paclitaxel and liposome forming materials are co-dissolved in organic solvent, solvent is evaporated to leave a thin dry film of lipid in drug and liposomes formed by addition of aqueous medium with vortexing and subsequent sonication to form small unilamellar vesicles (SUV's). Rahman et al further describe the incorporation of trehalose into the saline used to hydrate the thin film of the lipid and drug. The liposome suspensions were then stored by being frozen at −80° C. (without, apparently, being dried). The sugar-containing frozen liposome mixture is thawed and re-frozen and shown to be storage stable over several months. The mass ratio of sugar:lipid appears to be around 10–15:1.

Sharma, A. et al in Pharm. Res. 11(6) (1994) 889–896 describe encapsulation of paclitaxel (taxol) in liposomes formed from mixtures of phospholipids having an overall anionic charge. The lipids consist of mixtures of phosphatidylcholine and phosphatidylglycerol in various molar ratios. The liposomes are formed by co-dissolving paclitaxel and lipid in organic solvent, forming a thin film of the mixture, re-dissolving in butanol, freeze-dried, then rehydrating in aqueous rehydration medium. Incorporation of negatively charged phospholipid was said to reduce aggregation, and the liposomes were physically stable for more than two and a half months in the hydrated state, provided that the paclitaxel content was no more than 2 mole % (based on total lipid content). The authors indicate that precipitation of the drug in the organic solvent dissolution step caused instability and should be avoided.

Bernsdorff C. in J. Biomed. Mater. Res. 46 141–149 (1999) describe various investigations of the effect on liposome bilayers of paclitaxel. The drug appears to affect the fluidity of the bi-layer.

In U.S. Pat. No. 5,683,715 liposomes comprising a taxane comprise, as lipid, essentially only phosphatidylcholine. Examples of phosphatidylcholines are dioeoyl, palmitoyloleoyl or eggphosphatidylcholine. The liposomes may be provided in dehydrated form with protective sugars at the inside and outside surfaces of the bilayer. The general methods described for forming liposomes do not indicate how the taxane is to be incorporated into the liposomes. In the worked examples, paclitaxel is codissolved with lipid in cloroform or methylene chloride. To the mixed solution aqueous buffer is added followed by solvent removal to form multi-lamellar vesicles (MLV). Sonication, to form smaller vesicles resulted in precipitation of paclitaxel. None of the examples freeze dry the liposomal compositions and there is no disclosure of how to incorporate the cryoprotectant.

In U.S. Pat. No. 5,653,998, paclitaxel and other water insoluble compounds are formed into liposomal compositions which contain short chain fatty acids as stabilisers against flocculation. Sugars may be added as cryoprotectants. The formulations are formed by dispersing lipid and taxol directly into water using high energy mixing procedures, followed by filtration and high pressure homogenisation. After the active has apparently been encapsulated, a sugar may be added before freeze drying for cryoprotection. The freeze drying does not change the size of liposomes.

In WO-A-87/01933, amphotericin B, which is a lipophilic active, is formed into liposomal compositions. In one method, the active, sugar and lipid are all codissolved in an alcohol solution, which was dried then hydrated in buffer then freeze dried and rehydrated.

In WO-A-99/65465 methods are described for preparing liposomes by a dehydration/rehydration technique. A solution of lipid in an organic solvent is used to coat the inner surface of a suitable vessel and dried to form a thin film. The addition of an aqueous liposome forming liquid results in the formation of multi-lamellar liposomes which are subjected to a size control step to form small unilamellar vesicles (SUV's). Active ingredient may be co-dissolved with the lipid in organic solvent, may be present in the liposome forming liquid or may be mixed with preformed SUV's. The suspension of liposomes which contains active ingredient is subsequently dehydrated, by spray drying or, more usually, by freeze-drying (lyophilization). The dried mixture is subsequently rehydrated in an aqueous rehydration medium to form dehydration/rehydration vesicles (DRV's). The invention in WO-A-9965465 is to incorporate sugar in the suspension of liposomes prior to the dehydration step to increase the level of entrapment of hydrophilic active ingredients.

Merisko-Liversidge, E. et al in Pharm. Res 13(2) (1996) 272–278 describe alternative means for suspending lipophilic drugs in aqueous suspension media. Examples of lipophilic drugs are paclitaxel, camptothecin, etoposide and piposulfan. The active ingredients are wet milled in aqueous suspension containing stabiliser which is a nonionic surfactant. The final particle size was less than 400 nm.

According to the present invention there is provided a liposome forming process in which an aqueous suspension containing empty liposomes formed of liposome forming compounds, a lipophilic active ingredient and dissolved sugar is dehydrated.

The product of the dehydration step is a stable product which may be stored for later use. For instance the product may be used as such, for instance administered directly, for instance by inhalation. The dehydrated product may be used after admixture of a pharmaceutically acceptable solid excipient. More usually the dehydrated product is rehydrated before use either as part of a manufacturing step or as part of a medical practitioner's formulation.

In a preferred aspect of the present invention, the dehydrated product is rehydrated in an aqueous rehydration medium to form dehydration/rehydration vesicles (DRV's). In this aspect, the rehydration medium generally comprises a pharmaceutically acceptable aqueous medium, for instance water.

Following the rehydration step, the DRV's may be subjected to one or more size control steps. The DRV's in the rehydration medium may be subjected to physical mixing, sonication or homogenisation. However it is one advantage of the present invention, that the incorporation of sugar in the dehydration step results in the formation of DRV's which have sizes rendering them suitable for administration as a pharmaceutical without further size control steps. Preferably the final product, either of the rehydration step or of subsequent size control steps, has average diameter less than 1000 nm, most preferably substantially all the vesicles having sizes less than 1500 nm. More preferably the average diameter is less than 500 nm.

In the present invention, the weight ratio of sugar to liposome forming compounds in the dehydration step is preferably (at least 2):1. Preferably the ratio is (at least 5):1. The ratio may be (20 or more): 1, but is preferably (less than 20):1. These ratios are on a weight basis, of sugar to total liposome forming compounds.

In the present invention, the ratio of liposome forming compounds:active should be as low as possible. The invention enables ratios of (less than 10):1 to be achieved. Preferably the ratio is 7.5:(at least 1).

In the present invention, the liposomes in the aqueous suspension (before dehydration) are substantially empty of active compounds. They may contain buffer or other liquid excipient. The liposomes are thus formed from liposome forming compounds and aqueous medium in the absence of active ingredient in a previous step or are obtained as such from a commercial source. The liposomes should preferably be small unilamellar vesicles (SUV's) for instance having average diameter less than 500 nm preferably less than 200 nm, for instance in the range 50 to 100 nm. Suitable liposomes are commercially available, or may be produced in a previous liposome forming step using conventional techniques.

Where empty liposomes are used in the process, they are mixed with active ingredient in suitable form and optionally mixed by vortexing or homogenising. Since the active ingredient is lipophilic, it is unlikely to be soluble in the aqueous suspension at the concentration levels required for adequate levels required in the dried product. Suitable ways of dispersing the active ingredient into the aqueous suspension may be as described by Merisko-Liversidge et al (op.cit).

As an alternative to the wet milling process described by Merisko-Liversidge, the active ingredients may be subjected to a preliminary precipitate or colloid forming step in which it is dissolved in an organic solvent and re-precipitated or formed into a colloid by addition of a non-solvent for the compound, usually water. The precipitate may be collected and resuspended in the aqueous liposome suspension or a precursor aqueous liquid which is added to the remaining components for forming the said aqueous liposome suspension. It may be necessary for the active ingredient dispersion and/or the aqueous liposome suspension to be agitated throughout the process to keep the particles of active ingredient adequately dispersed. A colloidal suspension may be mixed directly with empty liposome suspension.

A preliminary step of forming a suitable precipitate or colloid of active ingredient involves dissolution of the ingredient in an alcohol or an ether. Preferably the alcohol or ether should be sufficiently volatile that it may be removed by evaporation from the precipitate prior to being incorporated into the aqueous liposome suspension. Alternatively the solid and liquid may be separated by centrifugation, with removal of the supernatant, followed by resuspension in water. In some circumstances, however, all of the solvent or a portion of it may remain with the precipitate of active ingredient whereby it remains in the liposome suspension and optionally also in the dehydrated product. The precipitate should have a volume mean diameter measured by a Malvern Mastersizers of about 1 μm to 100 μm preferably about 20–50 μm.

Where the organic solvent used to dissolve the active ingredient before precipitate or colloid formation is water-miscible, it may be unnecessary to recover the precipitate as a dry material before mixing with the liposomes suspension. In this case, the organic solvent may remain in the liposome suspension and/or in the dehydrated product, if the organic solvent is involatile. The presence of residual organic solvent may assist the incorporation of the lipophilic ingredient to the product vesicles. Preferably the organic solvent is substantially fully removed during processing, since it may interfere with the properties of the final vesicles. Thus preferably the aqueous suspension which is dehydrated is substantially free of organic solvent.

It is preferred to conduct a preliminary active ingredient precipitation step in which the active ingredient is dissolved in a suitable organic solvent, and is then precipitated therefrom by addition of a precipitant. The precipitate is separated from the liquid, preferably by centrifugation or filtration. The supernatant or filtrate is preferably discarded and the solid resuspended in non solvent.

Suitable organic solvents to dissolve the lipophilic active ingredient are alcohols, such as ethanol, or ethers or glycol ethers, such as low molecular weight polyethyleneglycols. The precipitant and resuspension medium are usually aqueous, preferably consisting of water alone.

The sugar used in the dehydration step may be a mono- or di-saccharide. Preferably it is a di-saccharide, for instance trehalose or, most preferably sucrose. The sugar should be fully dissolved in the aqueous suspension. This is generally achieved by forming a precursor solution of the sugar in water, although we have found that some sugars are sufficiently soluble in water that they may be added direct to the liposome suspension as particulate solid.

In the present invention the liposome forming compounds may have an overall charge, which may be positive or, preferably, negative. The use of such compounds may provide improved stability for dehydration rehydration vesicles in aqueous suspension. Anionic lipids are known and include phosphatidylserine and phosphatidylglycerol. It is preferred that the liposome forming compounds have no overall charge, and that each component has no overall charge. Preferably the liposome forming compounds include zwitterionic lipids, usually zwitterionic phospholipids such as phosphatidyl ethanolamine or, most preferably, phosphatidylcholine. The lipids generally comprise di-fatty acyl derivatives (that is esters), but may alternatively include the ether analogues. The fatty acyl groups are selected according to the desired fluidity, by selecting suitable chain lengths and presence, position and conformation of ethylenically unsaturated bonds in the chain. The liposome forming compounds may furthermore comprise cholesterol which may improve stability of the liposomes in the presence of plasma.

The present invention is suitable for encapsulating a range of lipophilic drugs such as those investigated by Meristo-Liversidge et al op. cit. It is of particular value for encapsulating paclitaxel and derivatives or analogues thereof (taxanes) which, as mentioned above, have particular problems which have proved hard to overcome. Other lipophilic drugs which, it is believed, may be usefully encapsulated in the invention include steroids, platinum-based drugs and non-steroidal anti-inflammatories.

The present invention is illustrated in the accompanying examples:

Materials

PC—Hydrogenated soya phosphatidyl choline is obtained from Lipoid

CHOL—Cholesterol is obtained from Sigma

DMPG—Dimyristoyl phosphatidylglycerol is obtained from Lipoid

DSPG—Distearoyl phosphatidylglycerol is obtained from Lipoid

DSPC—Distearoyl phosphatidylcholine is obtained from Lipoid

DSPE-PEG-PEGylated distearoyl phosphatidylethanolamine (PEG MW=2000) was a gift from Sequus EggPC—Egg phosphatidylcholine is obtained from Lipid products.

Paclitaxel is the drug used throughout the experiments. The $^3$H labelled pacitaxel is obtained from Moravek Biochemicals $^{14}$C labelled DOPE (dioleoyl phosphatidylcholine) is obtained from Amersham International.

Methods

SUV Formation

The liposome forming compounds in the desired ratios (as specified in the tables below) are co-dissolved in chloroform, used to form a thin film on the inner surface of a flask and dried, then water (as liposome forming aqueous medium) is added with vortexing to form multilamellar vesicles (MLV's). The MLV suspension is sonicated and metal particles removed by centrifugation. The SUV's have average diameter in the range 60 to 80 nm.

Dehydration and Rehydration Steps

The process is based on the method described by Kirby, C. and Gregoriadis, G. in Biotechnology 2(1984) 979–984. 2 ml of SUV is mixed with sugar in solid form and then active ingredient is added (in the ratios disclosed in the specific examples below) with vortexing, as necessary to avoid any components dropping out of the suspension. The suspension is subsequently cooled to a temperature of around −35° C. for 2–3 hours. Subsequently the frozen product is dehydrated at a high vacuum overnight.

The lyophilised cake is rehydrated in 100–300 µl of water (as rehydration liquor) to form DRV's. Samples were taken and the size of the vesicles determined by photon correlation spectroscopy using a Zeta sizer furthermore visual observations were made of the DRV suspension for signs of instability, through flocculation or other problems. Furthermore, the entrapment value for the paclitaxel is determined by observing $^3$H in the pellet and supernatant after centrifugation.

EXAMPLE 1

Optimising Sugar Level for High Lipid:Paclitaxel Ratio

In this example a solution of paclitaxel in ethanol is made up at a concentration of 20 mg/ml. An amount of the ethanolic paclitaxel solution is added to SUV's formed from the liposome forming compound specified in table 1, so as to form 1–4 ml of suspension (depending on the amount of lipid) containing 2 mg paclitaxel and 78 mg total lipid so as to form 4–5 ml suspension. Lipid ratios are molar. An aliquot of solid sucrose is also added using the general method (i.e. before the drug) so as to form a liposome suspension having the sucrose:lipid ratio specified in table 1.

The lipid suspension was subjected to lyophilisation and rehydration by the general technique described above. The DRV's were analysed to determine their average size and entrapment values.

The entrapment values were found to be 98 to 99%. The tests were carried out in duplicate and the results are shown in Table 1.

TABLE 1

| Example | Lipid Composition Mole Ratio | Sucrose Amount (g/g) (lipid) | Size nm |
|---|---|---|---|
| 1.1 | PC:CHOL:DMPG | 3 | 534 |
| | 1:1:0.1 | 3 | 529 |
| | Av (±SD) | | 531(2) |
| 1.2 | PC:CHOL:DMPG | 5 | 510 |
| | 1:1:0.1 | 5 | 440 |
| | Av (±SD) | | 475(35) |
| 1.3 | PC:CHOL:DMPG | 7 | 149 |
| | 1:1:0.1 | 7 | 131 |
| | Av (±SD) | | 140(9) |

EXAMPLE 2

Varying the Lipid Amount

In this example the total amount of paclitaxel and of sucrose remain the same. The amount of lipid is varied, but the experiment is otherwise as described in example 1 above. The entrapment levels are again found to be in the range 98 to 99%. The results are shown in table 2 below.

TABLE 2

| Example | Lipid Composition mole ratio Total Weight mg | Sucrose Amount (g/g) (lipid) | Size nm Comment |
|---|---|---|---|
| 2.1 | PC:CHOL:DMPG | 7 | 705 |
| | 1:1:0.1 | 7 | 364 |
| | 5 | | (particles non dispersed) |
| | Av (±SD) | | |

TABLE 2-continued

| Example | Lipid Composition mole ratio Total Weight mg | Sucrose Amount (g/g) (lipid) | Size nm Comment |
|---|---|---|---|
| 2.2 | PC:CHOL:DMPG | 7 | 274 precipitation |
|  | 1:1:0.1 | 7 | 350 precipitation |
|  | 10 |  |  |
|  | Av (±SD) |  |  |
| 2.3 | PC:CHOL:DMPG | 7 | 441 |
|  | 1:1:0.1 | 7 | 422 |
|  | 15 |  |  |
|  | Av (±SD) |  | 432(9) |
| 2.4 | PC:CHOL:DMPG | 7 | 590 |
|  | 1:1:0.1 | 7 | 727 |
|  | 20 |  |  |
|  | Av (±SD) |  | 658 (68) |

The results of examples 1 and 2 indicate that the ratio of sucrose to lipid should be optimised, as should the ratio of lipid to paclitaxel. The presence of ethanol in the dehydration stage and/or of paclitaxel appears to increase the ultimate size of the DRV's, where the ratio of lipid:drug is too low. The presence of sucrose appears not to improve the size to a large degree, although the stability of the DRV's is improved where the lipid:drug ratio is (more than 5):1.

EXAMPLE 3

In this example, the weight ratio of sugar:lipid is increased to 10 whilst the lipid components are varied. In each case the total lipid content is between 38 and 40 mg whilst the paclitaxel level stays as in examples 1 and 2, namely 2 mg. Entrapment values for all examples are in the range 98 to 99%. Other details are as in example 1. The results are shown in table 3.

TABLE 3

| Example | Lipid Composition Mole Ratio | Sucrose Amount (g/g) (lipid) | Size nm |
|---|---|---|---|
| 3.1 | PC:CHOL:DMPG | 10 | 566 |
|  | 1:1:0.1 | 10 | 389 |
|  | Av (±SD) |  | 478 (89) |
| 3.2 | DSPC:DSPG | 10 | Total aggregation |
|  | 1:0.2 | 10 | Total aggregation |
|  | Av (±SD) |  |  |
| 3.3 | DSPC:CHOL:DSPG | 10 | 573 |
|  | 1:1:0.1 | 10 | 559 |
|  | Av (±SD) |  | 566(7) |

The results in table 3 indicate that cholesterol improves the stability of the DRV's.

EXAMPLE 4

In this example the significance of the incorporation of anionic lipid is investigated by omission or reduction of the amount of PG or replacement by a PEGylated lipid. In all experiments, the level of lipid is between 38 and 40 mg whilst paclitaxel remains at 2 mg. The same general method as used in Example 1 is followed. Entrapment values were all in the range 98 to 99%. The results are shown in table 4.

TABLE 4

| Example | Lipid Composition Mole Ratio | Sucrose Amount (g/g) (lipid) | Size nm |
|---|---|---|---|
| 4.1 | PC:CHOL | 5 | 324 |
|  | 1:1 | 5 | 423 |
|  | Unstable |  | flocculation |
| 4.2 | DSPC:CHOL | 5 | 515 |
|  | 1:1 | 5 | 862 |
|  | Unstable |  | flocculation |
| 4.3 | DSPC:CHOL:DSPE-PEG | 5 | 755 |
|  | 1:1:0.05 | 5 | 817 |
|  | Unstable | Presence of particles | flocculation |
| 4.4 | PC:CHOL | 5 | 1656 |
|  | 1:0.5 | 5 | 2740 |
|  | Unstable |  | flocculation |
| 4.5 | DSPC:CHOL | 5 | 1506.8 |
|  | 1:0.5 | 5 | 2326 |
|  | Unstable |  | flocculation |
| 4.6 | DSPC:CHOL:DSPE-PEG | 5 | 805 |
|  | 1:0.5:0.1 | 5 | 1067 |
|  | Stable |  | 936(131) |
| 4.7 | PC:CHOL:DMPG | 10 | 247 |
|  | 1:1:0.01 | 10 | 417 |
|  | Av (±SD) |  | 332(85) |
| 4.8 | PC:CHOL:DMPG | 10 | 440 |
|  | 1:1:0.02 | 10 | 659 |
|  | Av (±SD) |  | 549(109) |
| 4.9 | PC:CHOL:DMPG | 10 | 484.7 |
|  | 1:1:0.05 | 10 | 346 |
|  | Av (±SD) |  | 415(69) |

Table 4 indicates that, for liposomes made by the general method disclosed in Example 1, the incorporation of anionic lipid appears to confer some stability against flocculation in the product. Reduction of the level of anionic lipid, down to 0.01 parts by mole based on one part of each of PC and cholesterol, still results in liposomes having adequate stability against flocculation. Removing the anionic lipid leads to an unstable suspension, from which the liposomes flocculate. Replacement of the anionic lipid by PEGylated lipid, which might be expected to confer resistance to flocculation, at relatively high levels (Example 4.6) confers some stability. However at the lower level of Example 4.3, the suspension is unstable.

EXAMPLE 5

Use of PEG300 as Vehicle for Drug

In this example, rather than dissolving the paclitaxel in alcohol, it is instead dissolved in an aqueous solution comprising 75% PEG having a molecular weight of 300, in 25% water. Two series of experiments were carried out, one using 100 µl of the 75% PEG solution, and the other using 100 µl of the paclitaxel solution in the 75% PEG solution, in each case added to SUV's in the same manner as the ethanolic paclitaxel solution is added to SUV's in Example 1. Thus the final suspension contains 2 mg paclitaxel and 75 to 80 mg total lipid. The remaining details are as in the general technique.

In each case the entrapment values paclitaxel were found to be around 98%. The lipid mixtures used, the amount of sucrose and the sizes of the produced DRV's are shown in table 5 below.

TABLE 5

| Example | Lipid Composition mole ratio | Sucrose Amount (g/g lipid) | Size nm without drug | Size nm with drug |
|---|---|---|---|---|
| 5.1 | PC:CHOL:DMPG 1:1:0.1 | 0 | 1033(133) | 2998(18) |
| 5.2 | PC:CHOL:DMPG 1:1:0.1 | 3 3 (no added PEG) | 201.4 68.3 | 806(17) |
| 5.3 | PC:CHOL:DMPG 1:1:0.1 | 5 | 123 | 500 |
| 5.4 | PC:CHOL:DMPG 1:1:0.1 | 7 | 104 | 466(51) |
| 5.5 | PC:CHOL 1:1 | 0 | 2540(20) | 2145 |
| 5.6 | PC:CHOL 1:1 | 3 | 703(98) | 794(72) |

The results in table 5 show clearly the effect on liposomes of the inclusion of sucrose for neutral and for anionic lipids, with and without drug, predissolved in PEG. This is the same general effect as illustrated above for methods in which the drug is dissolved in ethanol.

The results also show that increasing the level of sucrose results in a decrease in the DRV size, again with or without drug. The presence of drug seems to result in larger DRV.

EXAMPLE 6

In this example, a method similar to that used in Example 5 is used. That is the drug is predissolved in a 75% by weight PEG aqueous solution. In this experiment no comparison was carried out with PEG but without drug. In each experiment, the total level of drug used was 2 mg per experiment whilst the amount of lipid was in the range 38 to 40 mg (as compared to 75 to 80 used in Example 5). The lipid mixture is the same as used in Examples 5.1 to 5.4. In each case, the level of entrapment of paclitaxel was around 98 to 99%.

The results are shown in Table 6.

TABLE 6

| Example | Lipid Composition Mole Ratio | Sucrose Amount (g/g lipid) | Size nm |
|---|---|---|---|
| 6.1 | PC:CHOL:DMPG 1:1:0.1 Av ((±SD) | 5 5 | 561 560 560(1) |
| 6.2 | PC:CHOL:DMPG 1:1:0.1 Av (±SD) | 10 10 | 220 214 217(3) |

The results show that, for this system, the increase in the amount of sucrose provides further reduction in the DRV size.

EXAMPLE 7

In vivo Trials

Liposomes made according to the general technique and example 1, and including sucrose in an amount of 7 times by weight of the weight of the lipid, were made using the lipid mixtures, and ratios and the lipid weight:drug weight ratios indicated in Table 7 below (same compositions as Table 1). In order to provide a radio-active tracer in the paclitaxel and lipid, a trace of $^3$H-labelled paclitaxel and $^{14}$C labelled dioleoylphosphatidylethanolamine were used respectively. The 1 ml of DRV's were injected i.v. into rats (2 mg paclitaxel and 20, 40 or 78 mg lipid respectively). Samples of blood were taken from the animals after 2 minutes, 10 minutes, 60 to 80 minutes and 120 minutes and the level of $^3$H and $^{14}$C label detected. The total percentage of the lipid label and the paclitaxel label in plasma were calculated at the respective time intervals.

The results are shown in Table 7. As a comparison, a commercially available paclitaxel in Cremophor composition is used at the same dose level. (The commercially available paclitaxel has a trace of $^3$H label added).

TABLE 7

| | | | | % of injected dose | | | | | | | |
|---|---|---|---|---|---|---|---|---|---|---|---|
| | | | | 2 min | | 10 min | | 60–80 min | | 120 min | |
| Example 17 | formulation ratio/mole | Wt lipid/drug | Size nm | $^3$H | $^{14}$C | $^3$H | $^{14}$C | $^3$H | $^{14}$C | $^3$H | $^{14}$C |
| 7.1 | PC:CHOL:DMPG | 20 mg/2 mg | 276 | 12.9 | 56.7 | 7.3 | 35.6 | 0.34 | 22.7 | 0.17 | 33.5 |
| 7.2 | DSPC:CHOL:DSPG | 40/2 mg | 268 | 22.1 | 57.6 | 19.5 | 57.9 | 1.63 | 29.1 | 0.66 | 35.1 |
| 7.3 | PC:CHOL:DMPG | 78 mg/2 mg | 285 | 64.4 | 74 | 37.4 | 57.6 | 11.0 | 41.1 | 0.56 | 26.5 |
| Comp | Cremophor 49% ethanol | | | — | | | | | | 0.35 | — |

The animals were sacrificed after 2½ hours and the level of each label in the kidney(K), liver(L) and spleen(S) determined.

The results are shown in Table 8.

TABLE 8

| | Formulation molar | Lipid/drug | | % of injected dose | |
|---|---|---|---|---|---|
| Example | ratio | weight | | $^3$H | $^{14}$C |
| 7.1 | PC:CHOL:DMPG 1:1:0.1 | 20 mg/2 mg | K | 0.2 | 0.7 |
| | | | L | 34.33 | 22.13 |
| | | | S | 2.24 | 13.73 |
| 7.2 | DSPC:CHOL:DSPG 1:1:0.1 | 40/2 mg | K | 0.3 | 0.34 |
| | | | L | 19.3 | 20.36 |
| | | | S | 2.9 | 14.75 |

TABLE 8-continued

| Example | Formulation molar ratio | Lipid/drug weight | | % of injected dose $^3$H | $^{14}$C |
|---|---|---|---|---|---|
| 7.3 | PC:CHOL:DMPG 1:1:0.1 | 78 mg/2 mg | K | 0.54 | 0.9 |
| | | | L | 31.22 | 20.8 |
| | | | S | 2.83 | 13.20 |
| Comp | Cremophor and 49% ethanol | | K | 0.3 | |
| | | | L | 2.30 | |
| | | | S | 0.1 | |

The results in Table 7 appear to show that there is a dissociation between the lipid and the paclitaxel in the plasma over the period of the experiment. This is likely to be advantageous since it indicates that paclitaxel may be released following administration. The values in Table 8 show that the tissue distribution of the liposomal paclitaxel favours the liver and spleen, as compared to the prior art formulation.

EXAMPLE 8

Liposomes made as in Example 7 were composed as shown in Table 9. The lipid to drug mass ratios were 20:1. In order to provide a radioactive tracer in the paclitaxel and lipid, traces of $^3$H-labelled paclitaxel and $^{14}$C-labelled dioleoylphosphatidylcholine were used. The liposomes were injected into mice intravenously (0.33 mg paclitaxel and 8 mg lipid for each formulation). Samples of blood were taken at 5, 30, 60 and 180 minutes at which time the animals were killed. Paclitaxel ($^3$H) and lipid ($^{14}$C) radioactivities were measured in blood plasma samples, liver, spleen and kidneys and the percentage of the paclitaxel and lipid radiolabels in total plasma and tissues calculated at the respective time intervals. As a comparison, a commercially available paclitaxel (mixed with tracer $^3$H-labelled drug) Cremophor composition was used in the same dose level.

Figure 1:
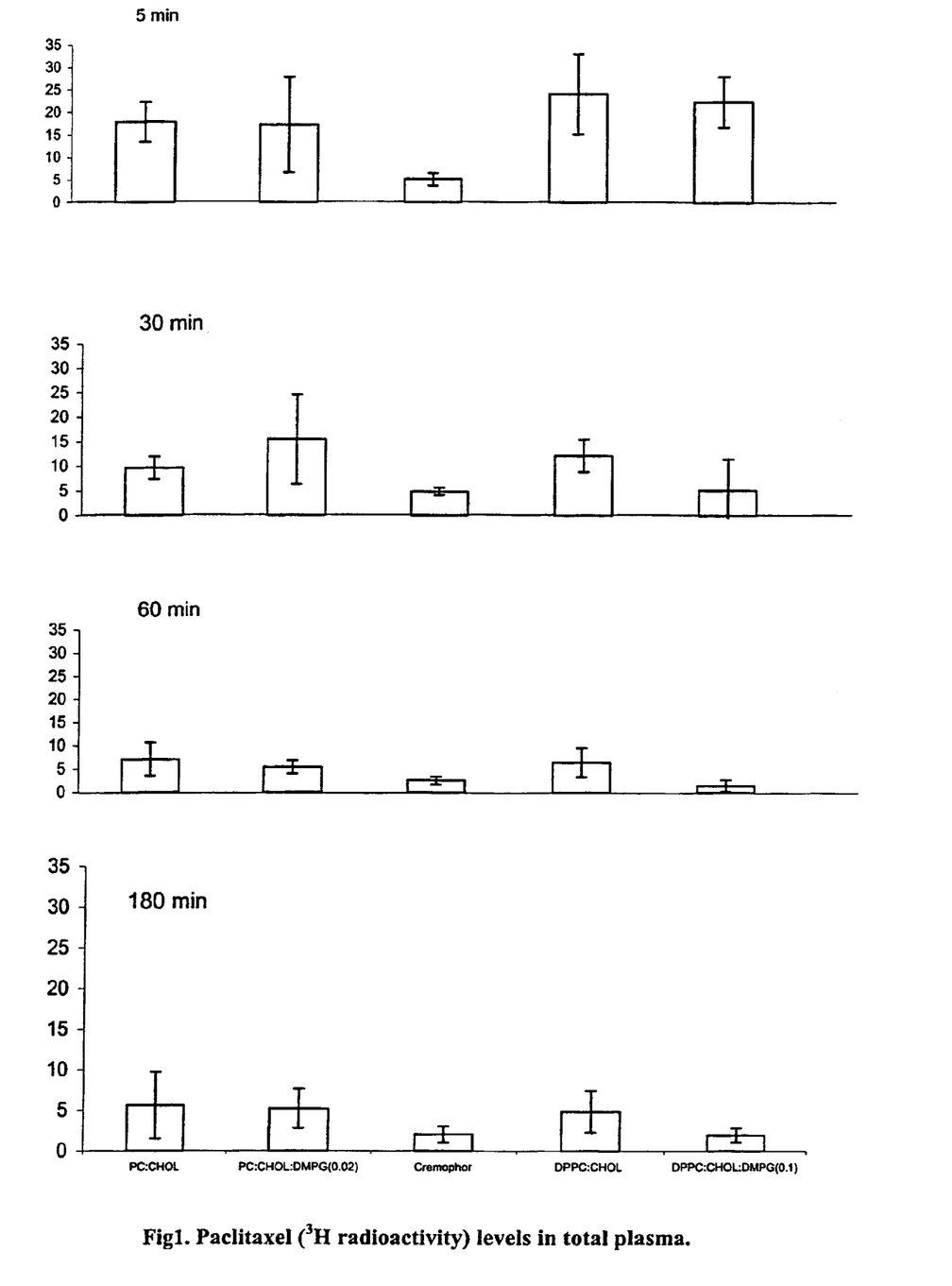
FIG. 1 shows the clearance of liposomal paclitaxel and paclitaxel in cremophor from the plasma.
Figure 2:
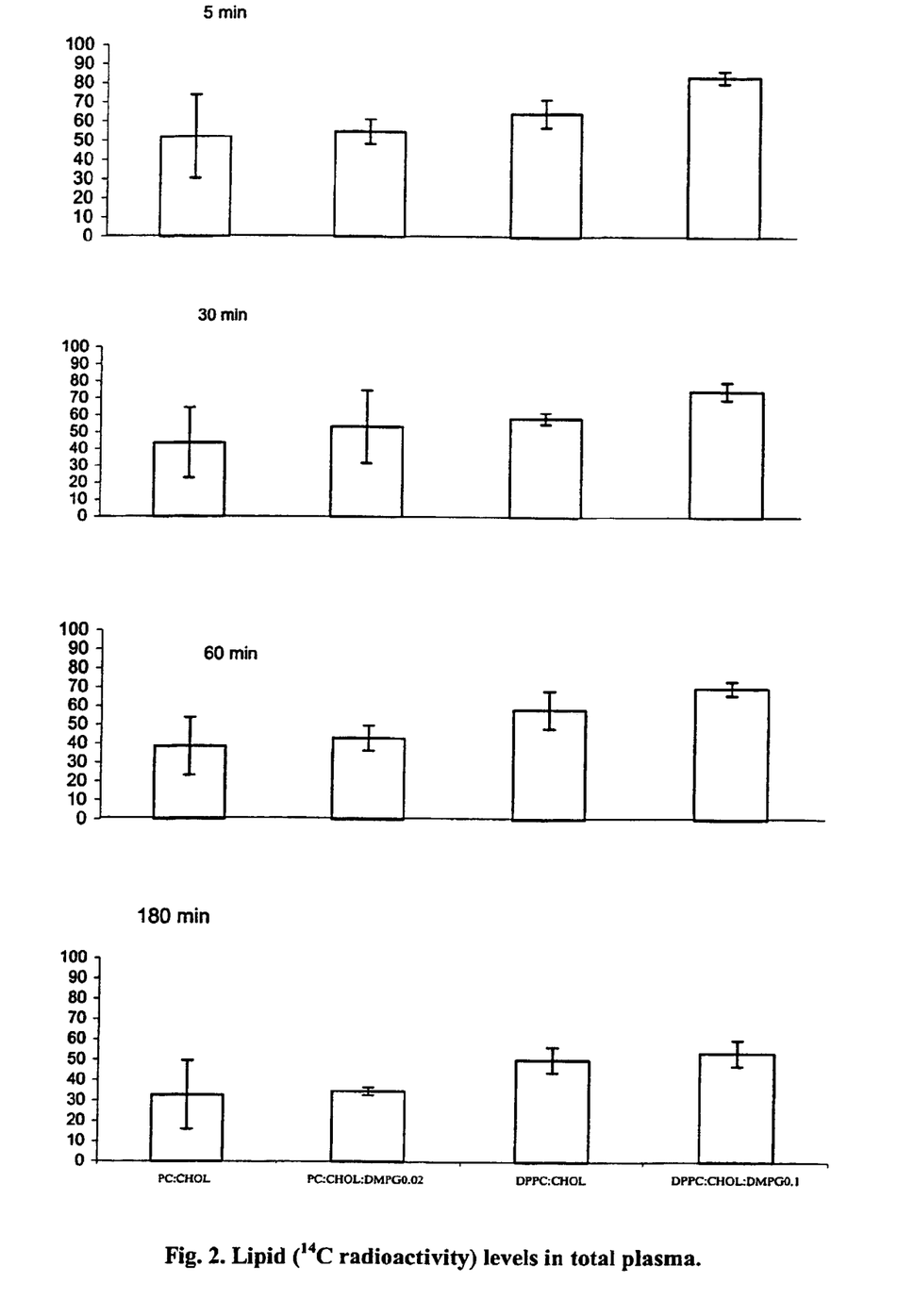
FIG. 2 shows the clearance of liposomes from the plasma.

The results are shown in FIGS. 1 and 2 and Table 9. FIGS. 1 and 2 demonstrate that clearance of liposomal paclitaxel (FIG. 1) from the plasma is more rapid than that of liposomes (FIG. 2), the implication being that there is a dissociation between the paclitaxel and liposomes in the plasma over the period of the experiment. FIG. 1 also shows that initial (at 5 min) clearance of paclitaxel in Cremophor is more rapid than that of paclitaxel in any of the liposomal formulations shown. Much of the paclitaxel given with liposomes ends up in the liver (L) and spleen (S) whereas lesser amounts of paclitaxel in Cremophor reach these tissues (Table 9). These results show that liposomes can alter the pharmacokinetics of the drug.

TABLE 9

| Example | Formulation molar ratio | Lipid/drug weight | | % of injected dose $^3$H | $^{14}$C |
|---|---|---|---|---|---|
| 8.1 | PC:CHOL(1.1) | 20:1 | Kidney | 2.4 | 1.0 |
| | | | Liver | 44.2 | 10.0 |
| | | | Spleen | 12.1 | 3.2 |
| 8.2 | PC:CHOL:DMPG (1.1:0.2) | 20:1 | Kidney | 2.5 | 1.1 |
| | | | Liver | 55.3 | 13.7 |
| | | | Spleen | 18.6 | 15.8 |
| 8.3 | DPPC:CHOL (1:1) | 20:1 | Kidney | 2.8 | 1.5 |
| | | | Liver | 60.1 | 15.9 |
| | | | Spleen | 14.4 | 5.3 |
| 8.4 | DPPC:CHOL:DMPG (1:1:0.1) | 20:1 | Kidney | 1.4 | 1.5 |
| | | | Liver | 79.4 | 16.7 |
| | | | Spleen | 11.6 | 6.8 |
| Comp | Cremophor and 49% ethanol | | Kidney | 1.4 | — |
| | | | Liver | 22.8 | — |
| | | | Spleen | 0.7 | — |

EXAMPLE 9

In this experiment, instead of dissolving the paclitaxel in alcohol and using the solution directly to add to SUV's, a preliminary paclitaxel precipitation step is carried out. Paclitaxel was solubilised in absolute ethanol at a concentration of 20 mg/ml. 600 μl of this stock solution (12 mg of paclitaxel) was added to 8 ml of distilled water. This resulted in is precipitation of paclitaxel, observed by the solution becoming cloudy. Paclitaxel precipitate was recovered from the suspension by centrifugation. The supernatant was removed and the pellet resuspended in 3 ml of distilled water.

500 μl of the redispersed paclitaxel (containing 2 mg paclitaxel) was added to a suspension of SUV's, followed by addition of sucrose, dehydration and rehydration following the rest of the general technique described above. In this experiment, the total amount of lipid in each case was 37 to 40 mg, whilst the ratio of sucrose to lipid is shown in Table 9 below, along with the lipid ratios.

TABLE 10

| Example | Lipid Composition Mole Ratio | Sucrose Amount (g/g) (lipid) | Size nm |
|---|---|---|---|
| 9.1 | PC:CHOL1:1 | 5 | 177 |
| | | 5 | 147 |
| | Average (SD) | | 162(15) |
| 9.2 | DSPC:CHOL1:1 | 5 | 143 |
| | | 5 | 137 |
| | Average (SD) | | 140(3) |
| 9.3 | PC:CHOL:DMPG 1:1:0.02 | 10 | 141 |
| | | 10 | 157 |
| | | | 149(8) |
| 9.4a | EggPC:CHOL | 10 | 313(6)(n = 3) |
| 9.4b | 1:1 | 10 | 294(2)(n = 3) |

The results show that, for preprecipitated paclitaxel, the DRV size is smaller for neutral lipid compositions (9.1 and 9.2). Example 9.3, using anionic lipid, also generates desirable low size DRV's. A direct comparison with the neutral lipid mixtures free of PEG is not possible, however, in view of the difference in the level of sucrose. The results of Example 9.4 indicate that, for lipid mixtures with a significant unsaturated acyl group content, the product DRV's have a useful size.

EXAMPLE 10

The general technique indicated in Example 9 for precipitating taxol prior to admixture with SUV's is followed except that, instead of using ethanol, a 75% by volume PEG/water mixture was used to dissolve the taxol (using the same concentration of 20 mg/ml). Furthermore 4 ml of water were used to precipitate 100 µl of solution. After the suspension had been left for one hour, centrifugation is performed to separate the precipitated paclitaxel. The supernatant is removed. The pellet is assessed for its taxol content and found to be around 99% of the originally added taxol. The pellet is redispersed in water, and the suspension mixed with SUV's, and solid sucrose, freeze dried and rehydrated as in the general technique. In each experiment the amount of lipid used for a 2 mg sample of paclitaxel is around 38 mg. The lipid mixtures and the sucrose:lipid ratio are shown in table 10 below.

In this example the size distribution of two repeats were determined with the standard deviation of the size determined for each sample. The results are also shown in the table.

TABLE 11

| Example | Lipid Composition mole ratio | Sucrose to lipid mass ratio (g/g) | Size (SD) (nm) |
|---|---|---|---|
| 10.1 | PC:CHOL:DMPG 1:1:0.02 | 10 10 Average (±SD) | 213(3) 198(1) 206(7) |
| 10.2 | PC:CHOL 1:1 | 10 10 Average (±SD) | 136 123 130(7) |
| 10.3 | DSPC:CHOL 1:1 | 10 10 Average ±SD | 122 143 133(11) |

The results illustrated in Table 11 show that PEG precipitation with recovery of the paclitaxel from the precipitant, again provides desirable results in terms of the DRV size. Good results are achieved both for neutral lipid mixtures and lipid mixtures having an overall anionic charge.

EXAMPLE 11

SUV's formed of equimolar soya bean phosphatidylcholine and cholesterol were made using the general technique described above. In order to confirm that liposomes were formed, two sets of experiments were conducted. In the first, the SUV's were mixed with carboxyfluorescein, dehydrated and rehydrated using the general technique described above including sugar in the SUV composition. In parallel, SUVs were mixed with carboxyfluorescein (CF) and paclitaxel, and dehydrated and rehydrated as described above with sugar in the SUV composition. The paclitaxel was in the form used in example 9. The percentage of CF encapsulated, and the Z average diameter were determined.

Where CF alone was encapsulated, the rate of encapsulation was about 12%. The Z average diameter was about 100 nm. For the coencapsulated CF and paclitaxel, the rate of encapsulation of CF was about 17%, whilst the Z average diameter was about 171 nm. The behaviour of the carboxyfluorescein in the coentrapped product was similar to that in which CF alone was entrapped. Since CF is well known to become entrapped into SUVs using this technique, it is reasonable to assume that the product of the process of the invention generates small vesicles containing paclitaxel.

In a separate test, the SUV's formed of equimolar soya bean PC and cholesterol were mixed with a precipitated paclitaxel, dehydrated and rehydrated using the same general method. The liposomes were recovered and observed under transmission electron microscope. The presence of lipid bilayers could clearly be observed in the DRV's.

The invention claimed is:
1. A liposome forming process comprising the steps:
   (a) forming a solution of a lipophilic active ingredient in a solvent;
   (b) adding to the resulting solution a precipitant which precipitates the active ingredient;
   (c) recovering precipitated particulate active ingredient;
   (d) resuspending the precipitated particulate active ingredient in an aqueous medium;
   (e) mixing an aqueous suspension of preformed empty liposomes having an average diameter less than 200 nm formed of liposome forming compounds which have an overall negative charge or have no overall charge with the resuspended particulate active ingredient;
   (f) dissolving sugar into the aqueous suspension of in an amount such that the weight ratio of sugar:liposome forming compounds is 5:1 to 20:1;
   (g) dehydrating the aqueous suspension containing empty liposomes, particulate active ingredient and dissolved sugar; and
   (h) rehydrating the dehydrated product in an aqueous rehydration medium to form dehydration/rehydration vesicles having an average diameter larger than the average diameter of the empty liposomes and less than 500 nm.
2. A process according to claim 1 in which the rehydration medium consists of water.
3. A process according to claim 1 in which the dehydration is carried out by spray drying or freeze drying.
4. A process according to claim 3 in which the liposome forming compounds comprise cholesterol and a phosphatidyl choline.
5. A process according to claim 1 in which the sugar is a mono- or di-saccharide.
6. A process according to claim 1 in which the liposome forming compounds comprise at least one nonionic or zwitterionic compound.
7. A process according to claim 1 in which the liposome forming compounds further comprise an anionic compound.
8. A process according to claim 1 in which the ratio of liposome forming compounds:active ingredient is less than 10:1.
9. A process according to claim 8 in which the ratio of liposome forming compounds:active ingredient is 7.5:at least 1.
10. A process according to claim 1 in which the empty liposomes in the aqueous suspension in step (e) have average diameter of less than 100 nm.
11. A process according to claim 1 in which the active ingredient is a taxane.
12. A process according to claim 11 in which the active ingredient is paclitaxel.
13. A process according to claim 1 in which the solvent is an alcohol, an ether or a glycol ether, and both the precipitant and the aqueous medium are water.
14. A process according to claim 13 in which the dehydration is carried out by freeze-drying.
15. A process according to claim 13 in which the solvent comprises ethanol or a low molecular weight polyethyleneglycol.
16. A process according to claim 15 in which the sugar is sucrose.
17. A liposome forming process comprising the steps:
   (a) dissolving an active ingredient which is a taxane in a solvent to form a solution of taxane;
   (b) adding to the solution of taxane a precipitant which precipitates the taxane;

(c) recovering the precipitated taxane from supernatant;
(d) resuspending the precipitated taxane in an aqueous liquid to form an aqueous suspension of taxane;
(e) mixing the aqueous suspension of taxane with preformed empty liposomes formed of liposome forming compounds to form a liposome and taxane suspension;
(f) dissolving sugar into the liposome and taxane suspension to form a sugar-containing suspension;
(g) dehydrating the sugar-containing suspension to form a dehydrated product; and
(h) rehydrating the dehydrated product in an aqueous rehydration medium to form liposomes which are dehydration/rehydration vesicles.

18. A liposome forming process comprising the steps:
(a) mixing an aqueous suspension of preformed empty liposomes formed of liposome-forming compounds with active ingredient which is a taxane in particulate form to form an aqueous suspension of liposomes containing taxane;
(b) dissolving sugar which is sucrose into the aqueous suspension of liposomes containing taxane;
(c) dehydrating the aqueous suspension containing empty liposomes, particulate active and dissolved sugar to form a dehydrated product; and
(d) rehydrating the dehydrated product in an aqueous rehydration medium to form liposomes which are dehydration/rehydration vesicles.

19. A liposome forming process comprising the steps:
(a) forming a solution of a lipophilic active ingredient in a solvent;
(b) adding a non-solvent to the resulting solution to form a colloidal solution of the active ingredient;
(c) mixing an aqueous suspension of preformed empty liposomes having an average diameter of less than about 100 nm and formed of liposome-forming compounds which have an overall negative charge or no overall charge with the colloidal solution of active ingredient to form an aqueous suspension of liposomes comprising active ingredient;
(d) dissolving sugar into the aqueous suspension of liposomes comprising active ingredient in an amount such that the weight ratio of sugar:liposome forming compounds is 5:1 to 20:1;
(e) dehydrating the aqueous suspension containing empty liposomes, active ingredient and dissolved sugar to form a dehydrated product; and
(f) rehydrating the dehydrated product in an aqueous rehydration medium to form liposomes which are dehydration/rehydration vesicles having an average diameter higher than the average diameter of the empty liposomes and less than 500 nm.

20. A process according to claim 19 in which the ratio of liposome forming compounds:active ingredient is less than 10:1 weight/weight.

21. A process according to claim 19 in which the active ingredient is a taxane and the sugar is sucrose.

* * * * *